United States Patent [19]

Lew

[11] Patent Number: 5,064,650
[45] Date of Patent: Nov. 12, 1991

[54] CONTROLLED-RELEASE SALT SENSITIVE CAPSULE FOR ORAL USE AND ADHESIVE SYSTEM

[75] Inventor: Chel W. Lew, San Antonio, Tex.

[73] Assignee: Southwest Research Institute, San Antonio, Tex.

[21] Appl. No.: 333,189

[22] Filed: Apr. 4, 1989

Related U.S. Application Data

[63] Continuation-in-part of Ser. No. 183,591, Apr. 19, 1988, abandoned.

[51] Int. Cl.$^5$ .......................... A61K 9/56; A61K 9/60
[52] U.S. Cl. ...................................... 424/435; 424/49; 424/401; 424/451; 424/461; 424/463
[58] Field of Search ............... 424/435, 463, 401, 461, 424/49, 451

[56] References Cited

U.S. PATENT DOCUMENTS

| | | | |
|---|---|---|---|
| Re. 33,093 | 10/1989 | Schiraldi et al. | 424/435 X |
| 3,015,128 | 1/1962 | Somerville Jr. | 425/5 |
| 3,092,533 | 6/1963 | Fisher Jr. et al. | 156/167 |
| 3,310,612 | 3/1967 | Somerville Jr. | 264/4 |
| 3,499,962 | 3/1970 | Wurzburg et al. | 424/489 |
| 3,520,971 | 7/1970 | Benford | 424/401 |
| 3,692,690 | 9/1972 | Horger | 427/213.33 |
| 3,798,179 | 3/1974 | Hellyer | 252/535 |
| 3,876,551 | 4/1975 | Laufer et al. | 252/98 |
| 3,896,033 | 7/1975 | Grimm, III. | 252/8.8 |
| 3,909,444 | 9/1975 | Anderson et al. | 428/402.24 |
| 3,911,099 | 10/1975 | Defoney et al. | 424/435 |
| 3,959,540 | 5/1976 | Leiberich et al. | 424/463 X |
| 4,124,521 | 11/1978 | Jedzinak | 252/127 |
| 4,149,978 | 4/1979 | Goffinet | 252/8.8 |
| 4,157,983 | 6/1979 | Golden | 427/213.34 |
| 4,166,800 | 9/1979 | Fong | 427/212 |
| 4,205,060 | 5/1980 | Monsimer et al. | 424/495 |
| 4,292,299 | 9/1981 | Suzuki et al. | 424/435 |
| 4,416,791 | 11/1983 | Haq | 252/90 |
| 4,849,227 | 7/1989 | Cho | 424/498 |

FOREIGN PATENT DOCUMENTS

| | | | |
|---|---|---|---|
| 838501476 | 2/1984 | European Pat. Off. | |
| 853008449 | 8/1985 | European Pat. Off. | |
| 8600280 | 11/1986 | European Pat. Off. | |
| 871164455 | 11/1986 | European Pat. Off. | |
| 863040440 | 12/1986 | European Pat. Off. | |
| 2132216 | 3/1972 | France | |
| 57-007408 | 1/1982 | Japan | 424/463 |
| 0833243 | 5/1981 | Sweden | 424/463 |
| 473890 | 7/1969 | Switzerland | |
| 931149 | 7/1968 | United Kingdom | |

OTHER PUBLICATIONS

SWRI, A Capability Statement for Micro Encapsulation, pp. 13-14, 19-23, pre-1988.

Primary Examiner—Thurman K. Page
Assistant Examiner—Robert H. Harrison
Attorney, Agent, or Firm—Vaden, Eickenroht, Thompson & Boulware

[57] ABSTRACT

A salt sensitive capsule has been developed which dissolves in the mouth and releases the encapsulated internal ingredient(s). The outer salt sensitive shell maintains its integrity when kept at a preselected aqueous salt concentrations. When introduced into the mouth, the degree of salinity is lower and causes the sheel to disassociated and release the internal component. The capsules may be associated with an adhesive system so that the capsules are topically applied to mouth tissue. The adhesive system is compatible with maintanance of the salt sensitive shell.

13 Claims, No Drawings

CONTROLLED-RELEASE SALT SENSITIVE CAPSULE FOR ORAL USE AND ADHESIVE SYSTEM

This application is a continuation-in-part of U.S. Ser. No. 7/183,591 with a filing date of Apr. 19, 1988 abandoned and entitled "Controlled-Release Capsules By The Use Of A Salt Sensitive Shell Material", Chel W. Lew, inventor.

BACKGROUND OF THE INVENTION

Encapsulation processes have been developed to make very small capsules containing a selected compound or mixture coated with a layer of another composition. The capsules can be in the size range of about 1 micron to several millimeters. The smallest capsules can be used in emulsion formulas. The smaller capsules are sometimes referred to as microcapsules.

Some microcapsules are designed to break under pressure so that the internal compound is released when rubbed over a surface. Microcapsules have been used containing therapeutic agents to be ingested coated with films broken down due to pH increases in the gastric system. Other films or shells on capsules are soluble in particular solvents. Release of the internal component is governed generally by solubility characteristics and the thickness of the shell.

The microcapsules are made by methods well known in art and have been used in various industrial and commercial applications. Typical processes are centrifugal extrusion, pan coating and air suspension methods. U.S. Pat. Nos. 3,692,690; 3,015,128 and 3,310,612 are exemplary of encapsulation techniques known and practiced in the art. In addition to those illustrated by the patents, other techniques are available. The present invention can utilize any of the available methods for preparing capsules or microcapsules.

SUMMARY OF THE INVENTION

The invention is a capsule for oral use containing an internal active ingredient which is coated with a shell of a non-toxic salt sensitive material. The salt sensitive capsules may be associated with an adhesion system. In this invention salt sensitivity relates to the integrity of the shell of the capsule or microcapsule in varying concentrations of salt in solution. The salt sensitive compositions are a rigid gel and insoluble when the salt level in an aqueous solution is maintained at a preselected level. Decreasing the level of salt by diluting the solution containing the capsules causes the salt sensitive shell to lose its structure, break down and dissolve. There are a number of polymers which are insoluble at certain preselected salt levels, depending on the polymer and salt used, and soluble at a lower salt levels.

The adhesive system associated with the salt sensitive encapsulated active ingredient does not affect the integrity of the capsule shell. The adhesive may be associated with the outer shell. The adhesive system may also be an adhesive in an aqueous gel with a salt concentration of the gel adjusted to the preselected level to maintain the integrity of the capsule shell.

The capsules are designed so that when they are placed in the human mouth with the normal salt (electrolytes) concentration, the capsules dissolve. The shell's composition can be formulated to provide slow or fast rate of dissolution. The capsules used with the adhesive system provide a mixture which can be placed inside the mouth on selected tissue. The capsules dissolve over a sustained period of time while the adhesion system holds them in place. The active ingredient is released over time in a specific region of the oral cavity.

The characteristics of the active ingredient to be enclosed must be considered in designing the capsule of this invention. A water soluble active ingredient is not to be encapsulated with a water soluble salt sensitive shell. If the active ingredient is water soluble, a water insoluble film layer must enclose the active ingredient which in turn is coated with the salt sensitive shell. There would be a two layer process for encapsulation so that the internal soluble ingredient will be protected from the salt sensitive shell with the water insoluble layer. The water insoluble layer is water dispersible so that the active ingredient is released once the capsule is placed in sufficiently diluted concentrations of salt to dissolve the salt sensitive layer exposing the water insoluble layer.

DETAILED DESCRIPTION OF THE INVENTION

The following description of the invention is for particular embodiments of capsules including microcapsules that can be used for oral medication. The invention is for a non-toxic, salt sensitive shell for release of an active ingredient such as medication or a breath freshener in the mouth. The active ingredient is contained inside the shell and is not released until the shell dissolves in the mouth. The alternative embodiment is the mixture of the capsules in a non-toxic adhesive system in which the bioadhesive is part of the outer shell of the capsules or the bioadhesive is a gel containing the capsules. The adhesive system is compatible with the salt sensitive shell such that the integrity of the shell is not affected by the adhesive.

A salt sensitive shell can be used in a single layer capsule to encapsulate a water insoluble ingredient. A water soluble active ingredient cannot be effectively encapsulated with a salt sensitive layer which reacts to water soluble compounds. Also, certain other active ingredients may be reactive with the compound or compounds selected for the salt sensitive shell. In instances where the internal component of the capsule cannot be in contact with the salt sensitive compound a non-toxic water insoluble and/or nonreactive layer of film encapsulates the internal component which in turn is coated with an outer shell of salt sensitive compound. The capsule has a two layer coating. The water insoluble compound should be water dispersible so that the active internal ingredient will be released in solution. The internal component of the capsule will be released upon the dissolution of the salt sensitive outer layer in a diluted salt concentration level and the following dispersal of the insoluble layer.

The capsules can be made as microcapsules using known encapsulation techniques such as centrifugal extrusion, pan coating and air suspension. The capsules of this invention include microcapsules and the broad categories of known capsules and encapsulation techniques The following Table 1 are examples of non-toxic salt sensitive materials. The materials are salted out of solution at a certain level of salt concentration and are insoluble. Table 1 has the maximum salt concentration for solubility. The mouth environment does not contain a high enough salt concentration to maintain the integrity of the capsules which would dissolve in the oral cavity.

TABLE 1*

| Salt Sensitive Material | Max. Salt Conc. for Solubility wt. % in sol'n of salt | | | |
|---|---|---|---|---|
| | NaCl | $Na_2SO_4$ | $Na_2CO_3$ | $Na_2PO_4$ |
| Polyvinyl alcohol (PVA) | 14% | 4% | 4% | 9% |
| Methyl Cellulose (MC) | 11 | 6 | 4 | 2.9 |
| Hydroxypropyl Methyl-(HPMC) Cellulose | 17 | 6 | 5 | 3.9 |
| Ethylhydroxyethyl-(EHEC) Cellulose | 8 | 2.5 | 3 | 3 |

*Information from Handbook of Water Soluble Gums and Resins by Robert L. Davidson (1980).

Other salt sensitive materials include polyethylene oxide and Carrageenan.

An example of non-toxic film for use with a water soluble internal component is oil base Span ®. The Span ® materials are partial esters of fatty acids and hexitiol anhydrides and the food grade acceptable Spans ® would be suitable. Also edible fats such as triglycerides would be suitable.

An example of a water insoluble compound used in this invention as the internal active ingredient is ethyl aminobenzoate. This compound, also known as benzocaine, is used as a local or topical anesthetic in the mouth. Benzocaine is relatively insoluble in water as one gram dissolves in about 2500 ml. Benzocaine is used at about 5% to 20% strength in a suitable carrier for anesthetics. For the purpose of this specification and claims, the water insoluble active ingredients can have some slight solubility in water such as benzocaine. Capsules of benzocaine are prepared using a salt sensitive shell. The shell is formulated to dissolve in the electrolyte concentration of the mouth releasing the benzocaine.

Other active ingredients to be encapsulated can be antibiotics capable of oral delivery such as bankcomycin, gentamicin, imipenem and ceptazidime. The antibiotics of this invention may be water soluble or water insoluble and are defined us oral antibiotics for the terminology of this invention.

The capsules may be included in an aqueous gel adhesive system which has a salt concentration of a preselected level high enough to maintain the integrity of the outer shell of the capsule surrounding the active ingredient. More than one active ingredient may be included inside the shell as long as the active ingredient does not adversely affect the shell by chemically reactivity or otherwise. For instance, a water insoluble flavoring oil may be mixed with the benzocaine for an oral anesthetic. The encapsulated component may be a mixture of ingredients. The active component can be any ingredient desired to be released in the mouth.

Examples of bioadhesives which can be used as a capsule coating or in a gel adhesive system are calcium polycarbophil, polyacrylic acid, gelatin, CMC, natural gums such as karaya and tragacanth, algin, chitosan, HPMC, starches, pectins and mixtures thereof. Compounds such as CMC or HPMC may have adhesive qualities as well as salt sensitivity. The adhesives are coated on the capsule shell or made part of the capsule shell provided there is compatibility with the shell composition to maintain integrity.

The adhesives may be mixed with a hydrocarbon gel base, composed of polyethylene and mineral oil, with a preselected salt level to maintain the capsule integrity.

The adhesive gel is adjusted to a preselected salt concentration with a non-toxic salt. The capsules are dispersed in the gel. The gel containing the capsules is applied to the tissue in the oral cavity where the delivery of the active ingredient is desired.

A typical bioadhesive aqueous gel system with benzocaine is comprised of CMC 1-30%, Pectin 1-5%, gelatin 0.1-10.0% and polyethylene (5% in mineral oil) 10-35%, and the remainder is water.

The adhesives of this invention allow the capsules to be placed in the mouth and adhere to the tissue in the oral cavity for a sustained period of time for delivery of the antibiotic, local anesthetic, breath freshener or other active ingredient.

What we claim is:

1. A capsule for oral use comprising:
   at least one internal active ingredient which is water soluble;
   a non-toxic water insoluble, water dispersible film layer surrounding said internal active ingredient;
   a non-toxic shell encapsulating said film surrounding the active ingredient and said shell is insoluble at a preselected salt concentration;
   said shell dissolving at a salt concentration present in the human mouth;
   said film dispersible in the human mouth; and
   a non-toxic adhesive system associated with the outer surface of said shell which permits adhesion of the capsule to selected tissue inside the mouth for a sustained period of time to allow for the dissolution of said shell and said film and release of the active component.

2. A capsule for oral medication of claim 1 wherein said water soluble ingredient is selected from the group consisting of water soluble antibiotics.

3. A capsule for oral use of claim 1 wherein said non-toxic water insoluble, water dispersible film layer is selected from the group consisting of food grade Span ® and edible fats.

4. A capsule for oral use of claim 1 wherein said non-toxic salt sensitive shell is selected from the group consisting of polyvinyl alcohol, methyl cellulose, hydroxypropyl cellulose, hydroxypropyl methyl cellulose, ethylhydroxyethyl cellulose, polyethylene oxide and Carrageenan.

5. A capsule for oral use of claim 1 wherein the non-toxic adhesion system is selected from the group consisting of calcium polycarbophil, polyacrylic acid, gelatin, CMC, natural gums, algin, chitosan, HPMC, starches, pectins and mixtures thereof which are applied to the outside of the shell of the capsules.

6. An oral usage formulation comprising:
   capsules made of at least one internal active water insoluble ingredient with a non-toxic shell encapsulating said internal active component which is insoluble at a preselected salt concentration with said composition of said shell dissolving at the salt concentration present in the human mouth and;
   said capsules contained in a non-toxic adhesive system such that the mixture of the capsules and the adhesive allows for the adhesion of the mixture to selected tissue inside the mouth for a sustained period of time to allow for the dissolution of the shell and the dispersal of the film layer and the release of the active ingredient.

7. An oral usage formulation of claim 6 wherein said non-toxic adhesive system comprising an aqueous gel with a salt concentration at a preselected level to maintain the integrity of the salt sensitive shell of the capsule.

8. The method of delivering an active ingredient to the oral cavity comprising the steps of:

encapsulating an active ingredient with an inner shell layer comprised of a water insoluble, water dispersible, nonreactive film layer to form a microcapsule;

further encapsulating the active ingredient with another layer comprised of a salt sensitive material which is insoluble at a preselected salt level in an aqueous solution to form a microcapsule with two layers around the active ingredient;

associating a plurality of microcapsule with an adhesive system which does not affect the integrity of the shell;

maintaining the integrity of the microcapsule by keeping the microcapsules in an aqueous solution having a salt concentration at which said salt sensitive material is insoluble soluble; and introducing the microcapsule having the adhesive system associated therewith into the oral cavity, the adhesive system causing the microcapsule to adhere to a selected site in the oral cavity for a sustained period of time, the salt concentration present in the oral cavity being lower than the threshold salt concentration at which the salt sensitive material is soluble such that the salt sensitive material comprising the outer layer of the microcapsule dissolves and the water dispersible layer dissolves, releasing the active ingredient at the selected site in the oral cavity.

9. The method of claim 28 additionally comprising encapsulating an active ingredient with an inner shell of a water insoluble, water dispersible film layer before encapsulating with salt sensitive material.

10. A delivery system for the oral cavity comprising a plurality of microcapsules with at least one active ingredient surrounded by an inner layer of a film of a water insoluble, water dispersible film and an outer shell that is insoluble at a preselected salt level in an aqueous solution and dissolves in the oral cavity;

an adhesive associated with the outer shell of the microcapsule which does not affect the integrity of the outer shell; and said adhesive causing adhesion of the microcapsules to the oral cavity for a sustained period of time to allow dissolution of the shell and release of the active ingredient.

11. A delivery system for the oral cavity of claim 10 comprising an inner layer of a film of a water insoluble, water dispersible, non-reactive film.

12. A microcapsule of claim 1 wherein said film layer is non-reactive with said active ingredient.

13. A microcapsule of claim 12 wherein said film layer is selected from the group consisting of oil based compounds and edible fats.

* * * * *

UNITED STATES PATENT AND TRADEMARK OFFICE
CERTIFICATE OF CORRECTION

PATENT NO. : 5,064,650
DATED : November 12, 1991
INVENTOR(S) : Chel W. Lew

It is certified that error appears in the above-identified patent and that said Letters Patent is hereby corrected as shown below:

Column 1, line 30, delete "in art" and substitute therefor --in the art--.

Column 3, line 40, delete "us" and substitute therefor --as--.

Column 3, line 48, delete "reactivity" and substitute therefor --reacting--.

Column 5, line 19, delete "soluble".

Column 6, line 3, delete "28" and substitute therefor --8--.

In the Abstract, lines 6 and 7, delete "disassociated" and substitute therefor --disassociate--.

In the Abstract, line 10, delete "maintanance" and substitute therefor --maintenance--.

Signed and Sealed this

Thirtieth Day of March, 1993

*Attest:*

STEPHEN G. KUNIN

*Attesting Officer*    Acting Commissioner of Patents and Trademarks